(12) United States Patent
Kashem

US012329453B2

(10) Patent No.: US 12,329,453 B2
(45) Date of Patent: Jun. 17, 2025

(54) DEVICE CALIBRATION VIA A PROJECTIVE TRANSFORM MATRIX

(71) Applicant: UNIVERSITY OF MIAMI, Miami, FL (US)

(72) Inventor: Rashed Kashem, Miami, FL (US)

(73) Assignee: University of Miami, Miami, FL (US)

( * ) Notice: Subject to any disclaimer, the term of this patent is extended or adjusted under 35 U.S.C. 154(b) by 950 days.

(21) Appl. No.: 17/392,664

(22) Filed: Aug. 3, 2021

(65) Prior Publication Data

US 2022/0125297 A1 Apr. 28, 2022

Related U.S. Application Data

(63) Continuation-in-part of application No. 17/246,054, filed on Apr. 30, 2021, which is a continuation of
(Continued)

(51) Int. Cl.
*A61B 3/024* (2006.01)
*A61B 3/00* (2006.01)
(Continued)

(52) U.S. Cl.
CPC .............. *A61B 3/024* (2013.01); *A61B 3/005* (2013.01); *A61B 3/032* (2013.01); *A61B 5/1114* (2013.01);
(Continued)

(58) Field of Classification Search
CPC ......... A61B 3/024; A61B 3/005; A61B 3/032; A61B 5/1114; A61B 2562/0219;
(Continued)

(56) References Cited

U.S. PATENT DOCUMENTS 10,531,795 B1 1/2020 Abou Shousha
2015/0062323 A1 3/2015 Gustafsson et al.
(Continued)

FOREIGN PATENT DOCUMENTS

WO 2019067779 A1 4/2019

OTHER PUBLICATIONS

International Search Report and Written Opinion issued in corresponding International Application No. PCT/US2021/054228 on Mar. 21, 2022 (14 pages).

*Primary Examiner* — Thomas K Pham
*Assistant Examiner* — Kuei-Jen L Edenfield
(74) *Attorney, Agent, or Firm* — Foley & Lardner LLP

(57) ABSTRACT

A method is disclosed for improving accuracy of visual field testing in head-mounted displays. The method includes retrieving a visual field testing pattern for a head-mounted display, the visual field testing pattern including stimuli displayed at respective locations in a visual field of the head-mounted display. The visual field testing pattern is generated on the head-mounted display. Data is retrieved from a tilt sensor, located at the head-mounted display, for detecting degrees of head tilt of a user wearing the head-mounted display and the degree of head tilt is determined. A comparison is made between the degree of head tilt of the user to a first threshold degree. In response to the degree of head tilt of the user meeting or exceeding the first threshold degree, a recommendation to the user is generated for display on the head-mounted display.

20 Claims, 14 Drawing Sheets

Related U.S. Application Data application No. 17/082,983, filed on Oct. 28, 2020, now Pat. No. 10,993,612.

(51) Int. Cl.
*A61B 3/032* (2006.01)
*A61B 5/11* (2006.01)
*G09G 5/38* (2006.01)

(52) U.S. Cl.
CPC ........ *G09G 5/38* (2013.01); *A61B 2562/0219* (2013.01); *G09G 2354/00* (2013.01); *G09G 2380/08* (2013.01)

(58) Field of Classification Search
CPC ... A61B 3/00; A61B 5/11; G09G 5/38; G09G 2354/00; G09G 2380/08; G09G 2340/0464; G06F 3/147; G02B 27/017; G02B 27/62; G02B 27/01
USPC ................. 351/224, 227, 222, 246; 345/7, 8
See application file for complete search history.

(56) References Cited

U.S. PATENT DOCUMENTS

| | | | |
|---|---|---|---|
| 2015/0310665 A1* | 10/2015 | Michail | G06F 3/013 345/419 |
| 2016/0371559 A1* | 12/2016 | Yang | G06V 10/245 |
| 2017/0307880 A1 | 10/2017 | Shrubsole et al. | |
| 2019/0150727 A1 | 5/2019 | Blaha et al. | |

* cited by examiner

1000

```
bitmap = new Calibration.Test.Bitmap( @"C:\image.jpg");

HUD.Display.PointF [] source = {
    new System.Drawing.PointF(0f, 0f),
    new System.Drawing.PointF(0f, bitmap.Height),
    new System.Drawing.PointF(bitmap.Width, bitmap.Height),
    new System.Drawing.PointF(bitmap.Width, 0f)};

HUD.Display.PointF [] target = {
    new System.Drawing.PointF(0f, 0f),
    new System.Drawing.PointF(0f, bitmap.Height),
    new System.Drawing.PointF(bitmap.Width * 0.75f, bitmap.Height - 50f),
    new System.Drawing.PointF(bitmap.Width * 0.75f, 80f)};

HUD.Display.Matrix matrix =
    HUD.Display.Transforms.Matrix.FromProjectivePoints(
    source, target);

HUD.Display.ApplyMatrixTransform transform =
    new HUD.Display.Transforms.ApplyMatrixTransform(matrix);

transform.ApplyTransform(bitmap);
```

FIG. 10

DEVICE CALIBRATION VIA A PROJECTIVE TRANSFORM MATRIX

CROSS REFERENCE TO RELATED APPLICATION(S)

This application is a continuation-in-part of U.S. patent application Ser. No. 17/246,054, entitled "Systems And Methods For Visual Field Testing In Head-Mounted Displays," filed Apr. 30, 2021, which is a continuation of U.S. patent application Ser. No. 17/082,983, filed Oct. 28, 2020, each of which is hereby incorporated by reference herein in its entirety.

BACKGROUND

Diagnosis of visual defects, such as blind spots, can be determined with conventional testing machines, such as a Humphry visual field analyzer. A patient is placed at the center of a curved portion of the analyzer and tests are performed by displaying images on the curved portion to determine where the blind spots are located in the patient's visual field. However, Humphry visual field analyzers as well as other testing machinery is both expensive for wide distribution and requires specialized personnel for operating the machinery.

SUMMARY

Accordingly, systems and methods are disclosed herein for the use of head-mounted display devices and/or head-mounted display devices for visual field testing. For example, these devices for visual field testing lowers the costs related to performing visual field testing and improves accessibility to visual field testing to a wider patient base. However, the adaption of visual field testing to these displays is not without its technical hurdles.

As a threshold technical problem, the introduction of visual field testing into head-mounted display devices must account for the effects of, or more accurately the lack thereof, of cyclotorsion. Cyclotorsion is the rotation of one eye around its visual axis. This rotation of the eye is what allows the visual field of a user to remain "right-side-up" even when the user tilts his or her head to one side or the other. However, as heads-up displays are fixed to the head of a user, cyclotorsion does not occur in the head-mounted display environment. That is, if a user tilts his or her head to one side or the other, the visual field of the user tilts accordingly. Thus, the effects of cyclotorsion present a threshold technical problem to overcome when adapting introducing visual field testing into head-mounted display devices.

As described herein, one solution to overcoming the technical problem caused by the differing effects of cyclotorsion in the head-mounted display environment is to prevent a user from tilting his or her head. However, conventional optometry tools for preventing a user from tilting his or her head such as chin rests, or other structures built into optometry equipment are ill-suited for a head-mounted display environment. First, a requirement for a specialized structure or modifications to head-mounted display devices negatively impacts the accessibility of the devices as well as their ease of use. Second, specialized structures such as chin rests do not prevent any tilting effects caused by the head-mounted display devices being improperly worn and/or worn in a manner that introduces a slight tilt.

Accordingly, the systems and methods disclosed herein may use specialized software and/or hardware elements implemented in the head-mounted display devices to detect a tilting head of a user. For example, the head-mounted display device may include specialized sensors and/or software used to interpret sensor data for the head-mounted display device. The systems and methods may further generate alerts to a user based on detected head tilting and/or recommendations for corrections of any head tilting. These alerts and recommendation may further be presented on the head-mounted display to minimize the impact of head tilts during visual field testing.

As a supplementary technical problem, even when the differing effects of cyclotorsion in the head-mounted display environment has been addressed, the adaption of visual field testing to head-mounted displays presents a secondary problem. Namely, visual field testing such as that performed by Humphry visual field analyzers is done by generating a series of white light stimuli of varying intensities (brightness), throughout a uniformly illuminated bowl. This illuminated bowl, or more precisely the illumination on a curved surface provides for standardized measurements of vison from a center of fixation in terms of degrees. However, head-mounted display devices do not provide for surfaces with a uniformed curvature. Instead, head-mounted display devices are generated on flat surfaces and/or surfaces with non-uniformed curvature. Accordingly, light stimuli appearing on a head-mounted display must account for these issues.

Methods, systems, and computer program products for improving accuracy of visual field testing in head-mounted displays are disclosed. In one aspect, a method can include retrieving a visual field testing pattern for a head-mounted display, wherein the visual field testing pattern comprises icons that are displayed at respective locations in a visual field of the head-mounted display. The method can also include generating for display the visual field testing pattern on the head-mounted display; retrieving data from a tilt sensor, located at the head-mounted display, for detecting degrees of head tilt of a user wearing the head-mounted display; determining, based on the data retrieved from the tilt sensor, a degree of head tilt of the user; comparing, the degree of head tilt of the user to a first threshold degree; and in response to the degree of head tilt of the user meeting or exceeding the first threshold degree, generating for display, on the head-mounted display, a recommendation to the user.

Another technical problem in conventional head-mounted displays is that calibrating a head-mounted display needs to compensate for unknown sources of error that may affect assessment of the calibration. For example, eye tracking data received during calibration would be affected if a head-mounted display was not being worn properly. This error (e.g., when the head-mounted display is used for an eye examination) could then be interpreted as a visual defect rather than knowing it was caused by improper wearing during calibration.

To address the above technical problems, the instant application discloses systems and methods that facilitate calibration of a head-mounted display. For example, the system may generate calibration patterns for the user to view while the system tracks the eye movement of the user to determine what they are seeing. The analysis of the eye tracking data can generate a calibration for the head-mounted display as well as a "calibration score" representing the accuracy of the calibration. In this way, an optical practitioner will have both the best possible calibration of a head-mounted display that may be used for eye examinations as well as a calibration score that may be indicative of the accuracy of an eye test performed with the calibrated head-mounted display.

Accordingly, methods, systems, and computer program products are disclosed for calibrating head-mounted displays. One method for calibrating a head-mounted display includes receiving edge eye tracking data during edge calibration periods; calculating a projective transform matrix based on the edge eye tracking data; receiving center eye tracking data during a center calibration period; applying the projective transform matrix to the center eye tracking data to determine a gaze location; and generating a calibration score based on a difference between a center location and the gaze location.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to particular implementations, it should be readily understood that such features are not intended to be limiting. The claims that follow this disclosure are intended to define the scope of the protected subject matter.

BRIEF DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings, FIG. 10 is illustrative pseudocode for calibrating a head-mounted display in accordance with certain aspects of the present disclosure.

DETAILED DESCRIPTION

The instant application describes systems and methods that facilitate performing visual field testing, particularly utilizing worn goggles that provide testing patterns. One problem confronting optical care practitioners is the effect of a patient tilting their head during eye examinations. If the head is tilted, this causes cyclotorsion, which is the rotation of one eye around its visual axis. Uncorrected, this can introduce error in an eye examination and misdiagnosis of optical issues. In the art, a conventional diagnostic device used for testing is a Humphry visual field analyzer "Humphry analyzer." Use of the Humphry analyzer includes a patient placing their head at the center of a semispherical region with testing patterns projected at varying locations of the semispherical region. With the development of Augmented Reality (AR) and Virtual Reality (VR) goggles, similar testing can be performed by projection of testing patterns upon the viewing surfaces of such goggles. As referred to herein, embodiments may use a heads up display device or a head-mounted display device. For example, a head-mounted display is a display device, worn on the head or as part of a helmet, that may have a small display optic in front of one (monocular HMD) or each eye (binocular HMD).

One technical problem is the occurrence of cyclotorsion in patients being tested using such goggles because while the goggles naturally provide compensation for head tilt, this only works if the goggles are worn properly (i.e., not tilted on the user's head). To address this problem, the instant application describes systems and methods for detection and correction of goggle tilt relative to the user's head. Another technical problem is the display of accurate testing patterns using the goggles, which have a flat viewing surface as compared to a Humphry analyzer, which has a curved viewing surface. To address this additional technical problem, methods are disclosed for generation of testing patterns in goggles that are equivalent to those generated in a Humphry analyzer.

Figure 1A:
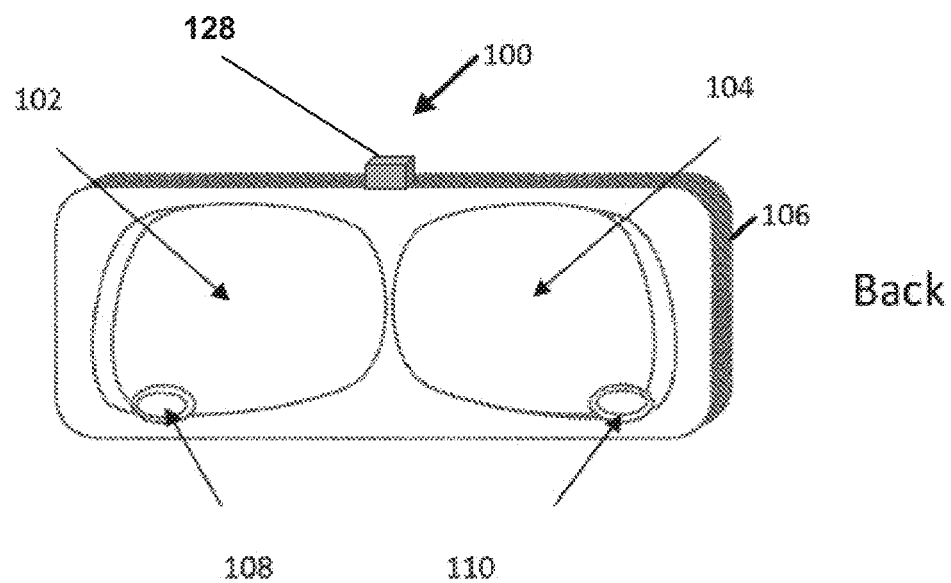
FIG. 1A illustrates an example head-mounted display forming a wearable device for a subject in accordance with certain aspects of the present disclosure.

FIG. 1A illustrates an example head-mounted display 100 (e.g., goggles) forming a wearable device for a subject. In some embodiments, the head-mounted display 100 may be a part of a visioning system as described herein or in U.S. patent application Ser. No. 17/083,043, entitled "Vision Testing via Prediction-Based Setting of an Initial Stimuli Characteristic for a User Interface Location" and filed Oct. 28, 2020, the contents of which are hereby incorporated by reference in its entirety. The head-mounted display 100 includes a left eyepiece 102 and a right eyepiece 104. Each eyepiece 102 and 104 may contain and/or associate with a digital monitor configured to display (or project) recreated images to a respective eye of the subject. In various embodiments, digital monitors may include a display screen, projectors, and/or hardware to generate the image display on the display screen. It will be appreciated that digital monitors comprising projectors may be positioned at other locations to project images onto an eye of the subject or onto an eyepiece comprising a screen, glass, or other surface onto which images may be projected. In one embodiment, the left eye piece 102 and right eyepiece 104 may be positioned with respect to the housing 106 to fit an orbital area on the subject such that each eyepiece 102, 104 is able to collect data and display/project image data, which in a further example includes displaying/projecting image data to a different eye.

In some embodiments, each eyepiece 102,104 may further includes one or more inward directed sensors 108, 110 may include infrared cameras, photodetectors, or other infrared sensors, configured to track pupil movement and to determine and track visual axes of the subject. The inward directed sensors 108, 110, e.g., comprising infrared cameras, may be located in lower portions relative to the eye pieces 102, 104, so as to not block the visual field of the subject, neither their real visual field nor a visual field displayed or projected to the subject. The inward directed sensors 108, 110 may be directionally aligned to point toward a presumed pupil region for better pupil and/or line of sight tracking. In some examples, the inward directed sensors 108, 110 may be embedded within the eye pieces 102, 104 to provide a continuous interior surface. In some embodiments, head-mounted display 100 can include tilt sensor(s) 128 that can provide data on the degree of head tilt to a connected computing system. As described further herein, the tilt sensors can be gyroscopes, water-based, etc.

Figure 1B:
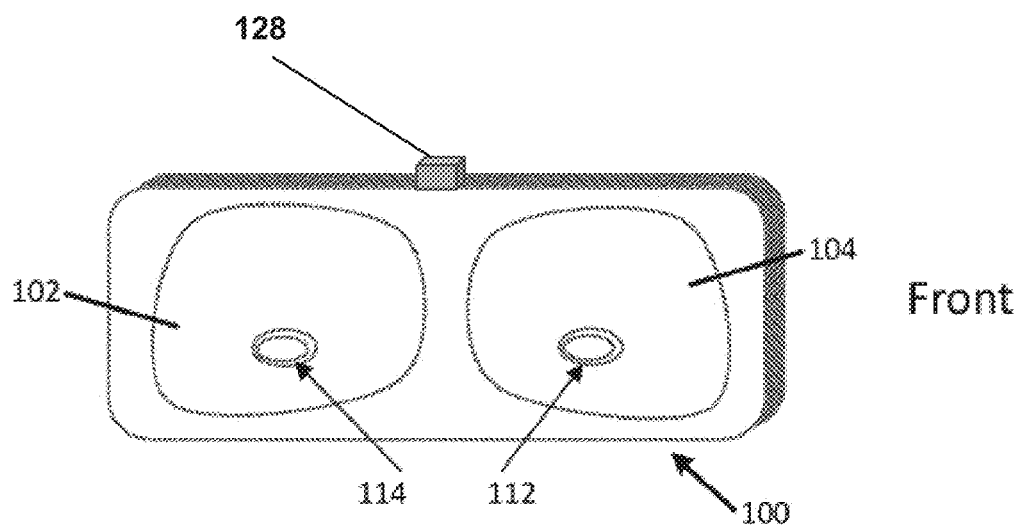
FIG. 1B illustrates a front view of the head-mounted display in accordance with certain aspects of the present disclosure, FIG. 1C an image of an example constructed head-mounted display in accordance with certain aspects of the present disclosure.

FIG. 1B illustrates a front view of the head-mounted display 100, showing the front view of the eye pieces 102, 104, where respective outward directed image sensors 112, 114 comprising field of vision cameras are positioned. In other embodiments, fewer or additional outward directed image sensors 112, 114 may be provided. The outward directed image sensors 112. 114 may be configured to capture continuous images.

Figure 1C:
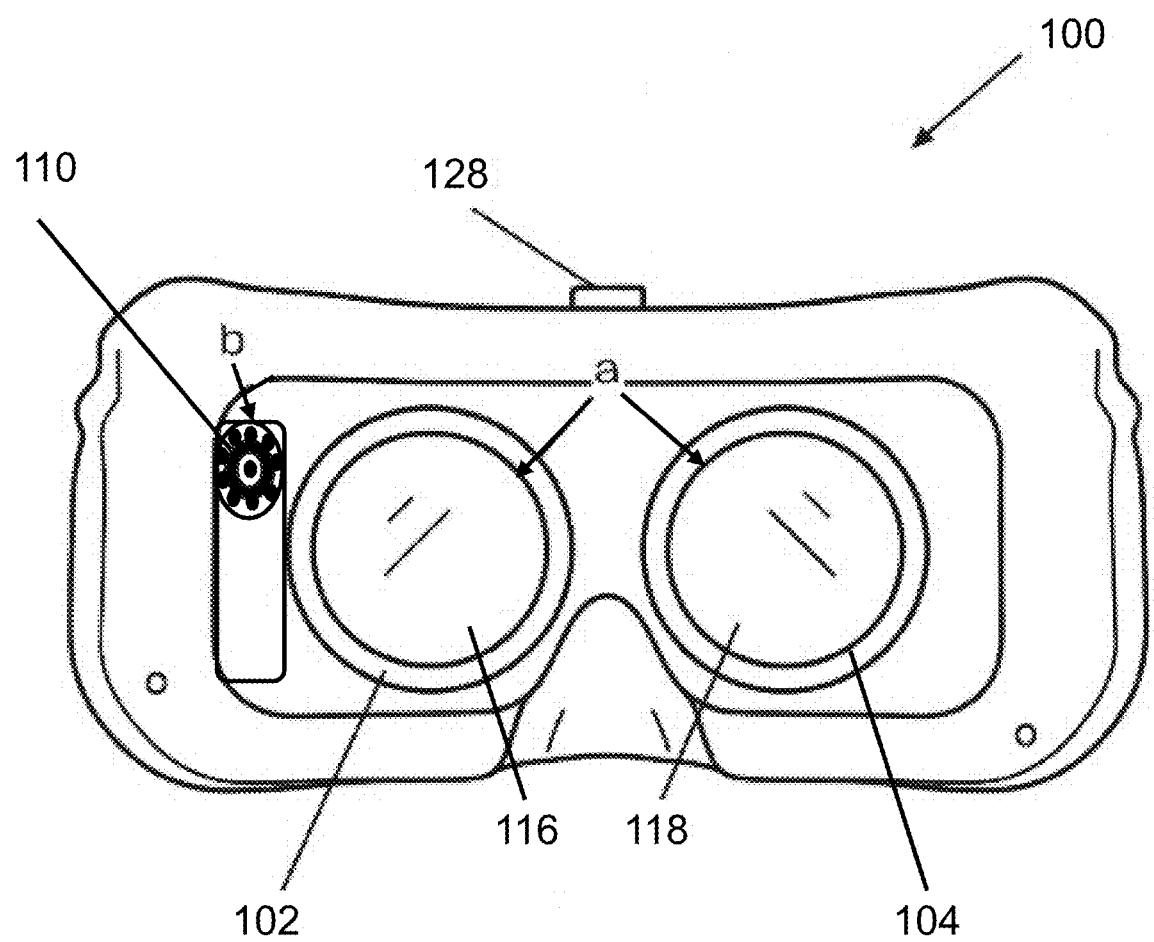
FIGS. 1D-1E illustrate another example embodiment of a head-mounted display, in accordance with certain aspects of the present disclosure.

FIG. 1C is an image of an example constructed head-mounted display 100 comprising eyepieces 102, 104 including two digital monitors, with focusing lens 116, 118. In this example, only one inward directed optical sensor 110 is included for pupil and line of sight tracking, however, in other examples, multiple inward directed optical sensors 110 may be provided.

Figure 1D:
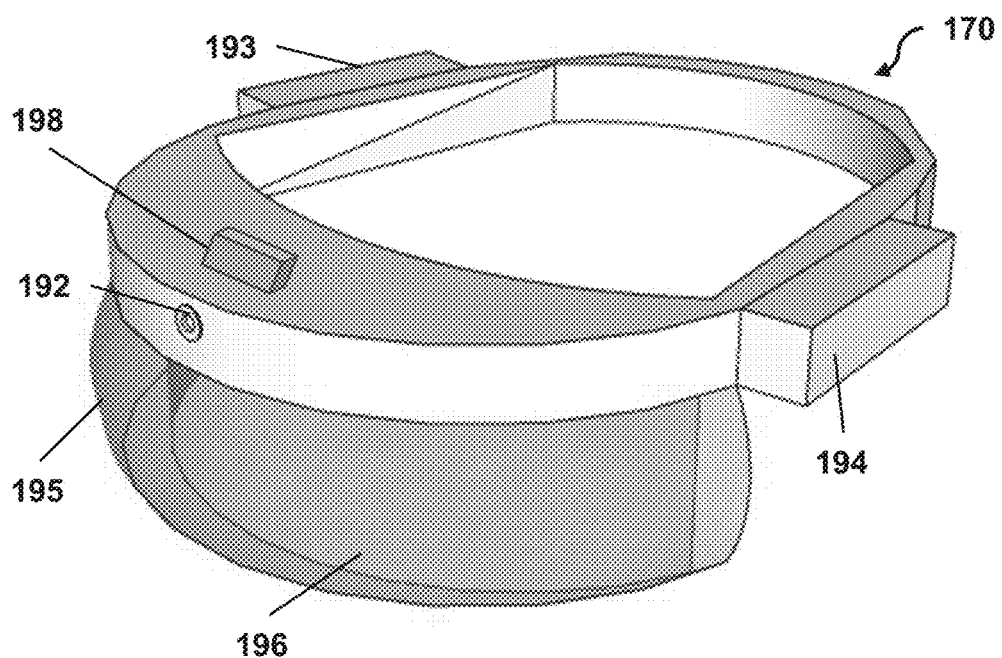
Figure 1E:
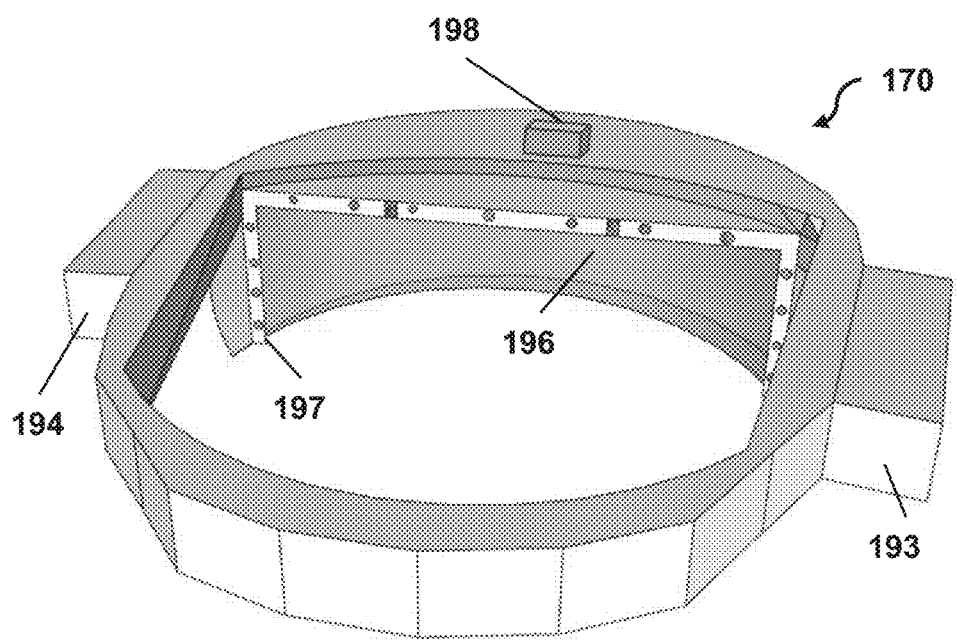

With respect to the FIGS. 1D-1E, an alternative embodiment of head-mounted 170 can include, in any combination, a high-resolution camera (or cameras) 102, a power unit 193, a processing unit 194, a glass screen 195, a see-through display 196 (e.g., a transparent display), an eye tracking system 197, tilt sensor(s) 198 (similar to tilt sensors 122), and other components.

In some examples, external sensors may be used to provide further data for assessing visual field of the subject. For example, data used to correct the captured image may be obtained from external testing devices, such as visual field testing devices, aberrometers, electro-oculograms, or visual evoked potential devices. Data obtained from those devices may be combined with pupil or line of sight tracking for visual axis determinations to create one or more modification profiles used to modify the images being projected or displayed to a user (e.g., correction profiles, enhancement profiles, etc., used to correct or enhance such images).

As used herein, when referring to the "head-mounted display," even where reference is made to the first embodiment (100), it is understood that the disclosed methods and operations apply to either head-mounted display 100 or 170, unless specifically stated otherwise. It should be noted that, although some embodiments are described herein with respect to calibration of head-mounted displays, such techniques may be applied for calibration of one or more other user devices in other embodiments.

The head-mounted display 100 may be communicatively coupled with one or more imaging processor through wired or wireless communications, such as through a wireless transceiver embedded within the head-mounted display 100. An external imaging processor may include a computer such as a laptop computer, tablet, mobile phone, network server, or other computer processing devices, centralized or distributed, and may be characterized by one or more processors and one or more memories. In the discussed example, the captured images are processed in this external image processing device; however, in other examples, the captured images may be processed by an imaging processor embedded within the digital spectacles. The processed images (e.g., enhanced to improve functional visual field or other vision aspects and/or enhanced to correct for the visual field pathologies of the subject) are then transmitted to the head-mounted display 100 and displayed by the monitors for viewing by the subject.

The head-mounted display can be used to perform a visual assessments to identify ocular pathologies, such as, high and/or low order aberrations, pathologies of the optic nerve such as glaucoma, optic neuritis, and optic neuropathies, pathologies of the retina such as macular degeneration, retinitis pigmentosa, pathologies of the visual pathway as microvascular strokes and tumors and other conditions such as presbyopia, strabismus, high and low optical aberrations, monocular vision, anisometropia and aniseikonia, light sensitivity, anisocorian refractive errors, and astigmatism.

In some examples, external sensors may be used to provide further data for assessing visual field of the subject. For example, data used to correct the captured image may be obtained from external testing devices such as visual field testing devices, aberromaters, electro-oculograms, or visual evoked potential devices. Data obtained from those devices may be combined with pupil or line of sight tracking for visual axis determinations to create the corrective profile of used to correct the images being projected of displayed to the viewer.

The head-mounted display 100 may be communicatively coupled with one or more imaging processor through wired or wireless communications, such as through a wireless transceiver embedded within the head-mounted display 100. An external imaging processor may include a computer such as a laptop computer, tablet, mobile phone, network server, or other computer processing devices, centralized or distributed, and may be characterized by one or more processors and one or more memories.

In an example operation of a vision system including the head-mounted display, real-time image processing of captured images may be executed by an imaging processor, e.g., using a custom-built MATLAB (MathWorks, Natick, MA) code, that runs on a miniature computer embedded in the head-mounted display. In other examples, the code may be run on an external image processing device or other computer wirelessly networked to communicate with the head-mounted display.

Figure 2:
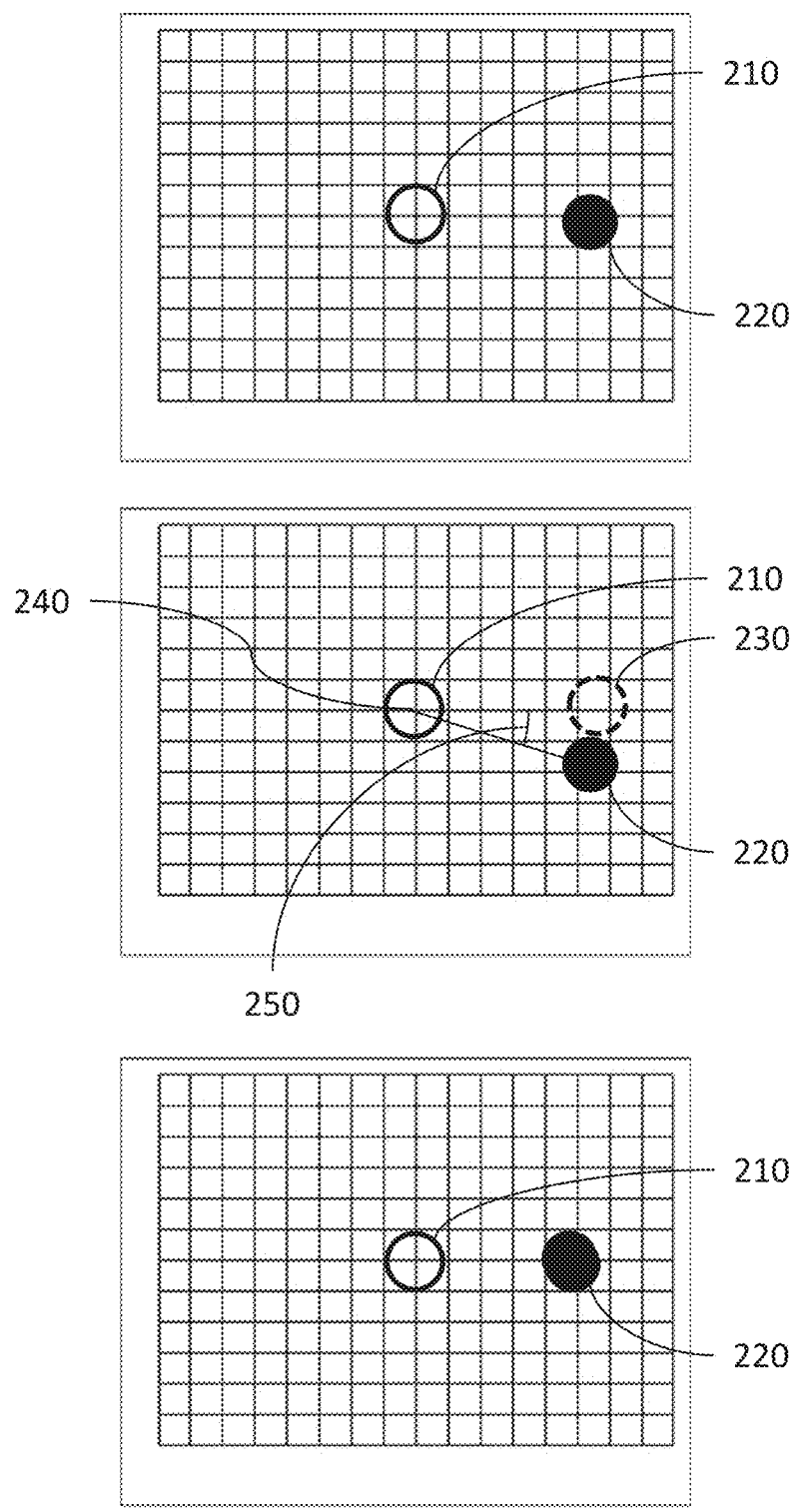
FIG. 2 is a diagram illustrating correction of a visual field testing pattern by detecting and correcting for head tilt in accordance with certain aspects of the present disclosure.

FIG. 2 is a diagram illustrating correction of a visual field testing pattern by detecting and correcting for head tilt. As used herein, the term "head tilt" refers to the angle between an axis of the head-mounted display and an axis of the user's head. For example, such an angle may be zero degrees when the head-mounted display 100 is worn correctly on the user. In an embodiment, a system for improving accuracy of visual field testing in head-mounted displays can include, in addition to the head-mounted display, a tilt sensor for detecting degrees of head tilt of a user wearing the head-mounted display. In some cases, the tilt sensor can be located at the head-mounted display 100, though tilt sensors at other locations (e.g., external ones such as cameras that view the user and the head-mounted display 100) are contemplated. In some embodiments, the tilt sensor can be a water-based tilt sensor, similar to a level. In other embodiments, the tilt sensor can incorporate a gyro sensor or other types of rotation sensing hardware.

In the head-mounted display 100, or on an external computer, storage circuitry can be configured to store and/or retrieve a visual field testing pattern having stimuli (e.g., lights, patterns, icons, animations, etc.) that can be displayed at respective locations in the visual field of the head-mounted display. There can also be control circuitry configured to generate for display the visual field testing pattern on the head-mounted display. Examples of a visual field testing pattern are shown in FIG. 2, with a fixation point 210 (typically near the center of the field of view) and a stimulus 220 that represents a displayed stimulus for determining the location of a blind spot. The top panel in FIG. 2 shows an example location of a blind spot (coincident with stimulus 220), e.g., as determined by the user being unable to see a stimulus displayed at that location. The middle panel illustrates the effect of head tilt. Here, the head tilt causes the stimulus 220 to be displayed at a different location in the user's vision, outside of the blind spot 230. As a result, the blind spot may not be identified by the user, possibly causing a misdiagnosis.

To address such issues, the system can determine, based on data retrieved from the tilt sensor, a degree of head tilt of the user. The degree of head tilt can be determined, for example in the case of a water-based tilt sensor, the determination of water surface that indicates the degree of tilt. One embodiment can include imaging a water surface with miniaturized cameras to capture the water surface relative to indicia that shows an un-tilted orientation. The angle between the water surface and the indicia would then be the degree of head tilt. Another embodiment can include obtaining data from a plurality of water sensors (e.g., galvanic sensors) that are covered or exposed by water depending on the degree of tilt. The particular sensors detecting water can then be used, such as via a lookup table, to determine the degree of head tilt. In some other embodiments, the degree of head tilt can be determined from received data from a gyroscope. The degree of head tilt of the user can be compared to a first threshold degree, such as 1, 2, 5, 10, degrees, or any threshold as desired. The comparison itself can include one or more processors receiving the calculated degree of head tilt and performing a numerical comparison to the first threshold degree. In response to the degree of head tilt of the user meeting or exceeding the first threshold degree, the system can generate for display, on the head-mounted display, a recommendation to the user for reducing the head tilt. Such a recommendation can include a visual indication (e.g., red or green lights, a textual indication, etc.) that the head-mounted display 100 needs to be adjusted to remove the head tilt. The recommendation can include a display of the degree of head tilt in, for example, a graphical format (e.g., depicting an angle) or textual format (e.g., the numerical value of the angle). After adjustment of the head-mounted display 100, testing can take place as shown in bottom panel of FIG. 2, showing that the stimulus remains at the proper location for detecting the blind spot in the user's field of vision.

In other embodiments, the system can automatically perform some corrections, e.g., if the tilt is relatively small.

Here, the control circuitry can be further configured to compare the degree of head tilt of the user to a second threshold degree (e.g., 0.1, 0.5, 1, 2 degrees, etc.) that is generally smaller than the first threshold degree. Such a second threshold degree can be reflective of asymmetry in a user's face that prevents perfect alignment, defects in the head-mounted display 100 construction, small incidental tilts occurring during measurements, etc. The comparison of the degree of head tilt to the second threshold degree can be performed in a manner similar to that described for the first threshold degree. In response to the degree of head tilt of the user meeting or exceeding the second threshold degree, the system can automatically adjust a respective location of the stimulus in the visual field of the head-mounted display by a first amount. For example, if a 0.1 degree tilt is detected, the system can automatically adjust the display location of the icon to compensate by changing the coordinates for display of the stimulus to reflect the detected tilt. In this way, the first amount can be based on a distance of the stimulus from a centerpoint 240 of the visual field of the head-mounted display and a direction of the head tilt of the user. In some embodiments, centerpoint 240 may correspond to a geometric center of the face of the head-mounted display 100 and/or a center of fixation of the user. For example, in some embodiments, different head-mounted displays may have different centerpoints. Accordingly, the system may determine the centerpoint of a head-mounted display and select respective locations of displayed icons based on the offset distance. For example, the system may determine a centerpoint of the head-mounted display based on receiving data from one or more sensors. Additionally or alternatively, the system may receive settings based on an initial calibration (e.g., an automatic calibration or a manual calibration) when the system is activated. Additionally or alternatively, the system may input a model or serial number (or other identifier) for the head-mounted display into a look-up table listing centerpoints for the model or serial number.

As shown in FIG. 2, centerpoint 240 can correspond to the center of the fixation point 210 and the direction 250 of the head tilt can be some angle (e.g., 10 degrees clockwise, 15 degrees, counterclockwise, etc.). Such a formulation permits a representation of the location of the icon relative to the center point (e.g., $\vec{r} = R \cos\theta \hat{x} + R \sin\theta \hat{y}$), where $\vec{r}$ is the vector from the center point to the icon having scalar distance R, which is unchanged regardless of head tilt. The terms are directional components (e.g., x/y, horizontal/vertical) of the vector $\vec{r}$ as a function of the head tilt angle θ. Thus, in an embodiment, the respective location of the icon can be defined by a first directional component (e.g., a horizontal component) and a second directional component (e.g., a vertical component). As shown in the bottom portion of FIG. 2, correction can include where the first directional component is adjusted by a cosine of the degree of head tilt of the user and the second directional component is adjusted by a sine of the degree of head tilt. For example, the system can determine the difference between the location of the icon before and after head tilt. This difference (for each directional component) can then be the amount (e.g., in pixels, cm, etc.) by which the respective location of the icon can be adjusted.

Figure 3:
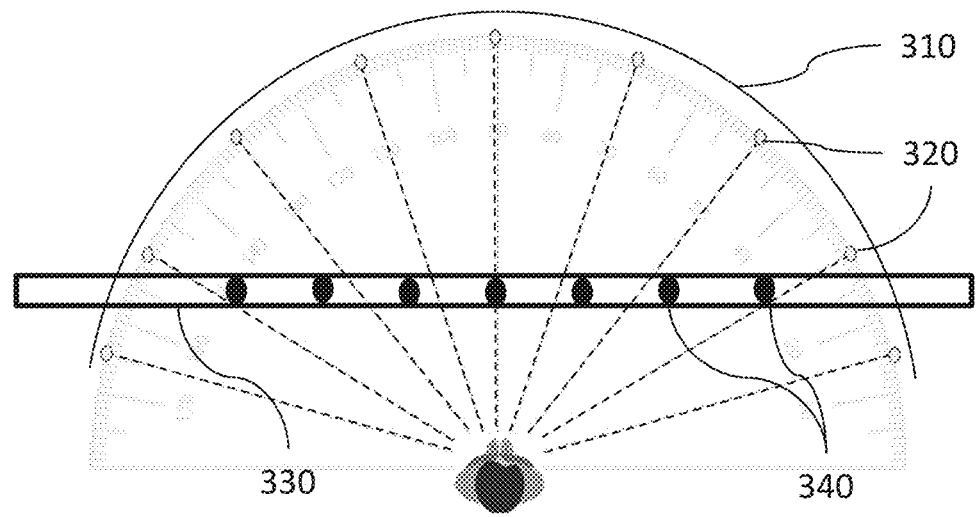
FIG. 3 is a diagram illustrating an exemplary method of accurately replicating a visual field testing pattern from a curved surface on a flat surface in accordance with certain aspects of the present disclosure.
Figure 3:
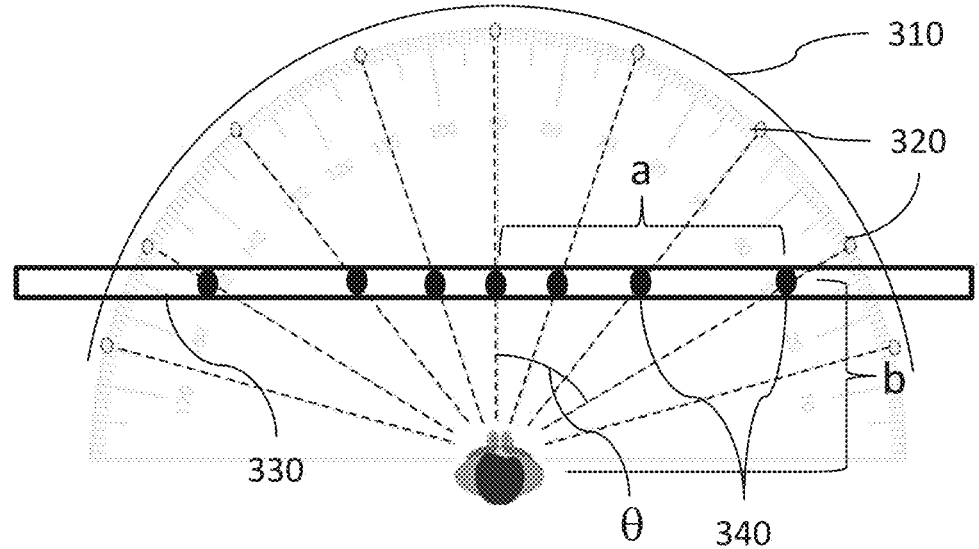

FIG. 3 illustrates a simplified diagram depicting an exemplary method of accurately replicating a visual field testing pattern from a curved surface on a flat surface. Determining an angle of a visual defect can be important in diagnosing and treating it. The Humphry analyzer, with its semispherical testing region 310, as depicted in FIG. 3 (top) can provide a visual field testing pattern in the form of visual elements 320 at angles of constant separation (e.g., 10, 20, 30, 40, etc. degrees). However, the head-mounted display 100 can have a flat surface 330 (shown simplified and greatly enlarged, for illustrative purposes). If stimuli 340 are displayed at equidistant locations as shown, they will not conform to the constant angular separation as described above with the Humphry analyzer, and thus not characterize the user's vision accurately. Accordingly, the system may compensate for this difference.

Another consideration is that the offset distance (dimension b in the bottom of FIG. 3) between the flat surface where stimuli are displayed and the eye of the user can vary, based on the particular construction of the head-mounted display 100, a user's facial structure, etc. This offset distance can in turn affect where the stimuli 340 need to be displayed.

As shown in FIG. 3 (bottom), the disclosed methods allow respective locations of the stimuli 340 to be located in a row on the visual field and correspond to respective projections of points corresponding to different viewing angles along a curved surface onto a flat surface. This is depicted in FIG. 3 as can be seen by the stimuli 340, at their respective locations, being intersected by radial lines from visual elements 320. The respective locations can be determined based on an offset distance of the head-mounted display and an angle to respective points on the visual testing machine. The angle can be that referred to above, (e.g., 10, 20, 30 degrees, etc.). Given the angle and the offset distance, the respective location corresponding to it is shown by dimension a, which is the distance from the center (e.g., 0 degrees) to the respective location on flat surface 330. As one example, the respective locations can be determined based on the expression in Equation 1, $$a = b\sqrt{\frac{1}{\cos^2\theta} - 1}, \quad (1)$$

where a is one of the respective locations, b is the offset distance, and θ is the angle.

While several simplifying assumptions have been taken for the purpose of explanation, it is understood that a person of skill would be able to incorporate variations in accordance with the present disclosure, for example, accounting for the fact that each eye is off center (as opposed to the single viewing point assumed in FIG. 3), that the flat surface may indeed not be perfectly flat, but may contain some slight curvature (e.g., as depicted in FIGS. 1A and 1B), etc. Thus, as used herein, a "flat" surface is assumed to be the special case of a curved surface having an infinite radius of curvature. As described in some portions herein, the head-mounted display can have a finite radius of curvature and thus be "curved" in the traditional sense.

In some implementations, the curvature of the head-mounted display can be determined, and the respective locations selected, based on the curvature. The determination of the curvature can be known or accessed based on data from a known model of head-mounted display. Such curvature values can be stored for retrieval or accessed via a network connection. The exact relation of how the presence of curvature affects the shifting of the respective location is a function of the geometry of the system. Thus the disclosed methods contemplate a coordinate transformation from the intended angle θ to, for example, an analogous angle φ that represents the angle along the curved surface of the head-mounted display which would appear to the user to be at the intended angle.

Also, while the present disclosure has described visual field testing patterns generally located on a horizontal "row," it is contemplated that the disclosure applies to patterns that may be at an angle, vertical, or anywhere in a 2D plane. Similarly, such features can be extended to 3D visualizations, such as by altering the placement (and optionally size) of the stimuli to give a depth effect, similar to a heads-up-display.

Figure 4:
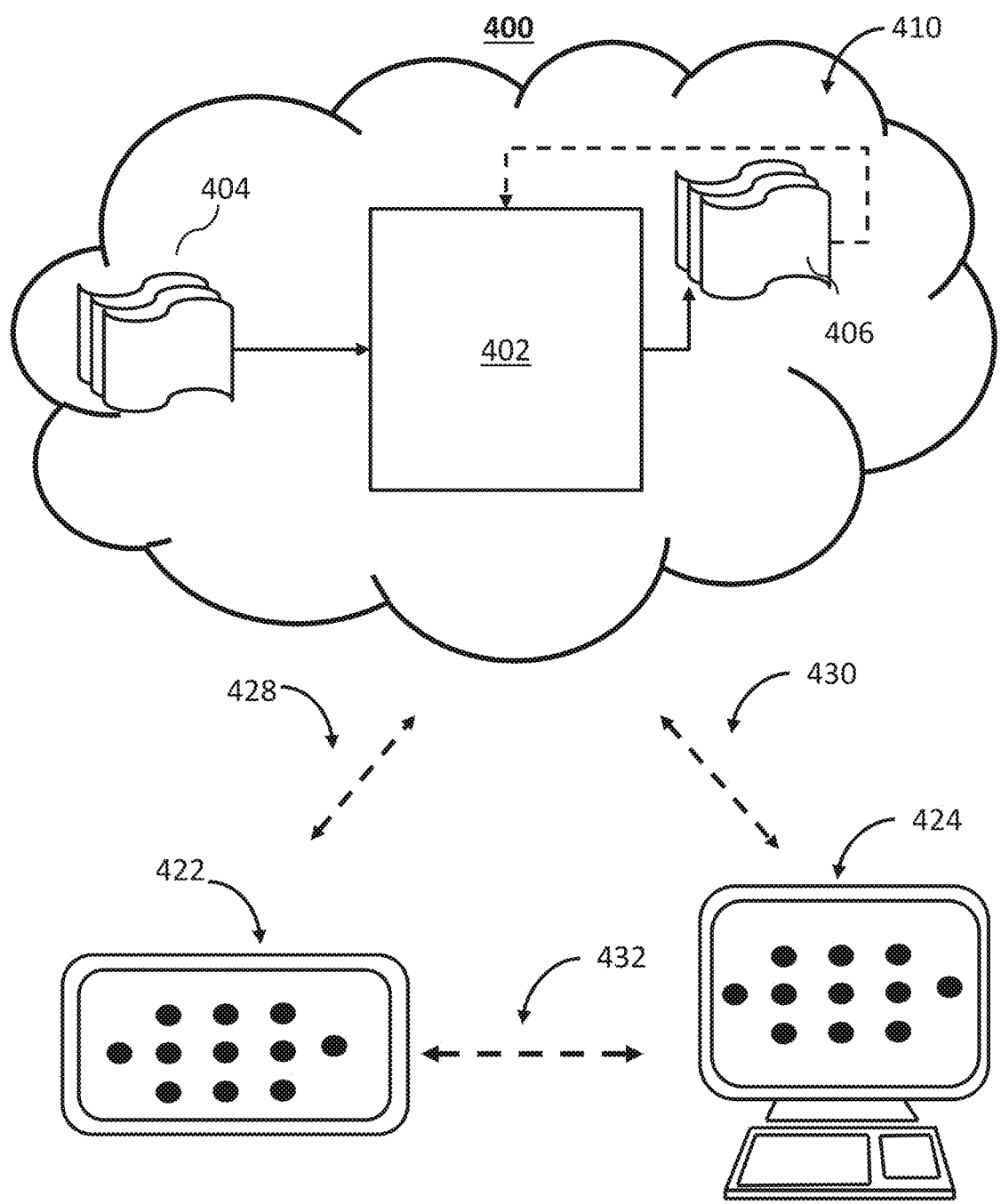
FIG. 4 is an illustrative system diagram for visual field testing using a head-mounted display in accordance with certain aspects of the present disclosure.

FIG. 4 is an illustrative system diagram for visual field testing using a head-mounted display, in accordance with one or more embodiments. For example, system 400 may represent the components used to power the head-mounted displays of FIGS. 1A-1C and perform the processes described in FIGS. 5-6. As shown in FIG. 4, system 400 may include heads up display device 422 and user terminal 424. For example, heads up display device 422 may be worn by a user, while progress of the user may be monitored via user terminal 424. It should be noted that heads up display device 422 and user terminal 424 may be any computing device, including, but not limited to, a laptop computer, a tablet computer, a hand-held computer, other computer equipment (e.g., a server), including "smart," wireless, wearable, and/or mobile devices. FIG. 4 may also include additional components such as cloud components 410. Cloud components 410 may alternatively be any computing device as described above and may include any type of mobile terminal, fixed terminal, or other device. For example, cloud components 410 may be implemented as a cloud computing system and may feature one or more component devices. It should also be noted that system 400 is not limited to three devices. Users, may, for instance, utilize one or more devices to interact with one another, one or more servers, or other components of system 400. It should be noted, that, while one or more operations are described herein as being performed by particular components of system 400, those operations may, in some embodiments, be performed by other components of system 400. As an example, while one or more operations are described herein as being performed by components of mobile device 422, those operations, may, in some embodiments, be performed by components of cloud components 410. In some embodiments, the various computers and systems described herein may include one or more computing devices that are programmed to perform the described functions. Additionally, or alternatively, multiple users may interact with system 400 and/or one or more components of system 400. For example, in one embodiment, a first user and a second user may interact with system 400 using two different components.

With respect to the components of head-mounted display device 422, user terminal 424, and cloud components 410, each of these devices may receive content and data via input/output (hereinafter "I/O") paths. Each of these devices may also include processors and/or control circuitry to send and receive commands, requests, and other suitable data using the I/O paths. The control circuitry may comprise any suitable processing, storage, and/or input/output circuitry. Each of these devices may also include a user input interface and/or user output interface (e.g., a display) for use in receiving and displaying data. For example, as shown in FIG. 4, both head-mounted display device 422 and user terminal 424 include a display upon which to display data (e.g., a visual field test pattern).

It should be noted that in some embodiments, the devices may have neither user input interface nor displays and may instead receive and display content using another device (e.g., a dedicated display device such as a computer screen and/or a dedicated input device such as a remote control, mouse, voice input, etc.). Additionally, the devices in system 400 may run an application (or another suitable program). The application may cause the processors and/or control circuitry to perform operations related to visual field testing.

Each of these devices may also include electronic storages. The electronic storages may include non-transitory storage media that electronically stores information. The electronic storage media of the electronic storages may include one or both of (i) system storage that is provided integrally (e.g., substantially non-removable) with servers or client devices, or (ii) removable storage that is removably connectable to the servers or client devices via, for example, a port (e.g., a USB port, a firewire port, etc.) or a drive (e.g., a disk drive, etc.). The electronic storages may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. The electronic storages may include one or more virtual storage resources (e.g., cloud storage, a virtual private network, and/or other virtual storage resources). The electronic storages may store software algorithms, information determined by the processors, information obtained from servers, information obtained from client devices, or other information that enables the functionality as described herein.

FIG. 4 also includes communication paths 428, 430, and 432. Communication paths 428, 430, and 432 may include the Internet, a mobile phone network, a mobile voice or data network (e.g., a 5G or LTE network), a cable network, a public switched telephone network, or other types of communications networks or combinations of communications networks. Communication paths 428, 430, and 432 may separately or together include one or more communications paths, such as a satellite path, a fiber-optic path, a cable path, a path that supports Internet communications (e.g., IPTV), free-space connections (e.g., for broadcast or other wireless signals), or any other suitable wired or wireless communications path or combination of such paths. The computing devices may include additional communication paths linking a plurality of hardware, software, and/or firmware components operating together. For example, the computing devices may be implemented by a cloud of computing platforms operating together as the computing devices.

Cloud components 410 may be a database configured to store user data for a user. For example, the database may include user data that the system has collected about the user through prior transactions. Alternatively, or additionally, the system may act as a clearing house for multiple sources of information about the user. Cloud components 410 may also include control circuitry configured to perform the various operations needed to generate recommendations. For example, the cloud components 410 may include cloud-based storage circuitry configured to store a first machine learning model that is trained to detect head tilt, adjust visual testing patterns, and/or generate recommendations. Cloud components 410 may also include cloud-based control circuitry configured to determine an intent of the user based on a machine learning model. Cloud components 410 may also include cloud-based input/output circuitry configured to generate the dynamic conversational response during a conversational interaction.

Cloud components 410 includes machine learning model 402. Machine learning model 402 may take inputs 404 and provide outputs 406. The inputs may include multiple datasets such as a training dataset and a test dataset. Each of the plurality of datasets (e.g., inputs 404) may include data subsets related to user data and visual testing patterns. In some embodiments, outputs 406 may be fed back to machine learning model 402 as input to train machine learning model 402 (e.g., alone or in conjunction with user indications of the accuracy of outputs 406, labels associated with the inputs, or with other reference feedback information). For example, the system may receive a first labeled feature input, wherein the first labeled feature input is labeled with a testing pattern adjustment for the first labeled feature input. The system may then train the first machine learning model to classify the first labeled feature input with the known testing pattern adjustment.

Figure 5:
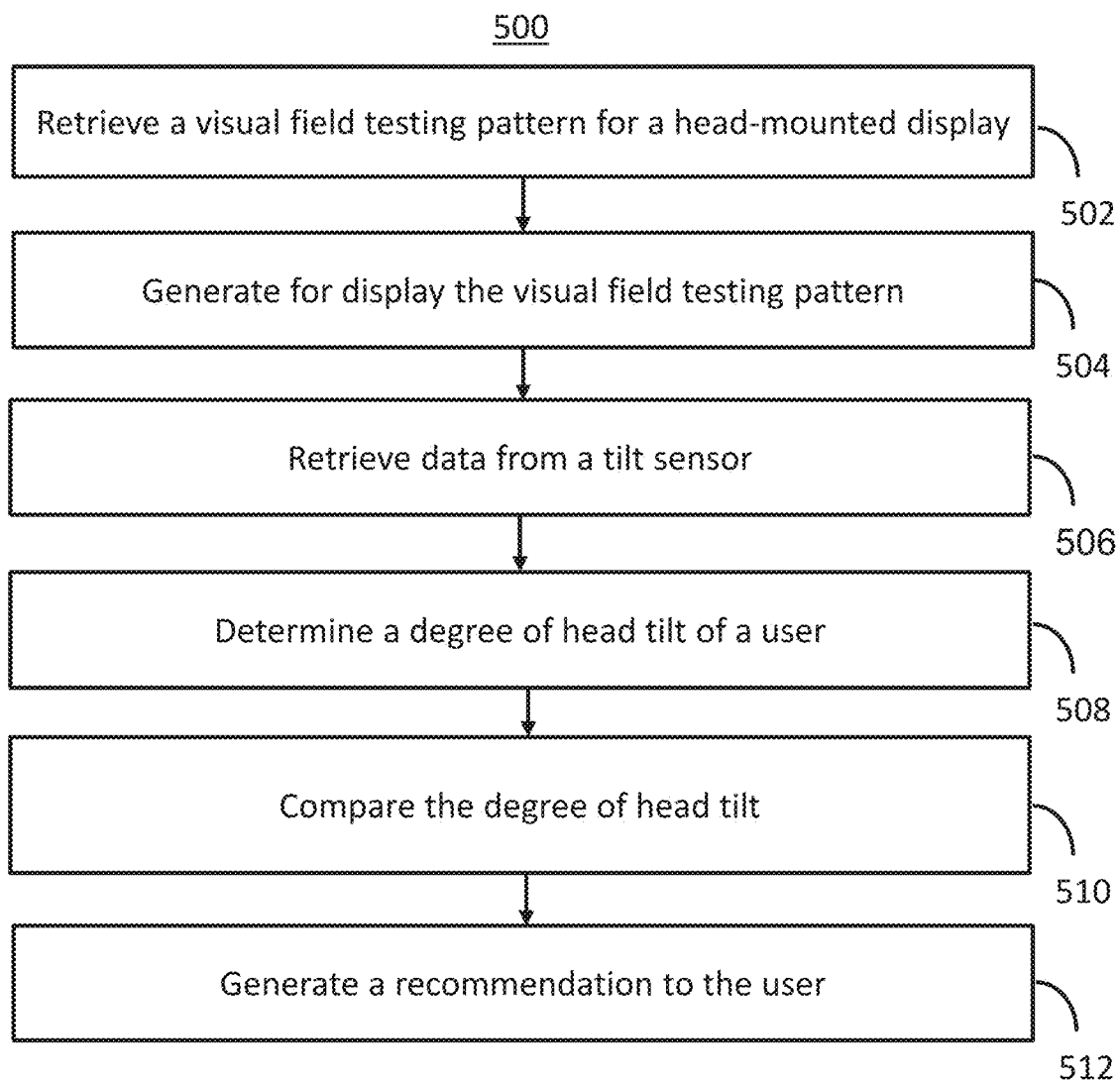
FIG. 5 is a process flow diagram for correction of a visual field testing pattern by detecting and correcting for head tilt in accordance with certain aspects of the present disclosure.

FIG. 5 is a process flow diagram for correction of a visual field testing pattern by detecting and correcting for head tilt. For example, process 500 may represent the steps taken by one or more devices, as shown in FIGS. 1A-1C, when providing visual field testing using a head-mounted display.

At step 502, process 500 (e.g., using one or more components in system 400 (FIG. 4)) retrieves a visual field testing pattern for a head-mounted display. For example, the system may retrieve a visual field testing pattern for a head-mounted display, wherein the visual field testing pattern comprises stimuli that are displayed at respective locations in a visual field of the head-mounted display. In another example, the respective location of the icon can be defined by a first directional component and a second directional component. The first directional component can be adjusted by a cosine of the degree of head tilt of the user and the second directional component can be adjusted by a sine of the degree of head tilt of the user.

In yet another example, the respective locations of the stimuli can be located in a row on the visual field and the respective locations can correspond to respective projections of points corresponding to different viewing angles along a curved surface onto a flat surface. Also, in other examples, the respective locations can be determined based on an offset distance of the head-mounted display and an angle to respective points on the visual testing machine. Accordingly, in some examples, the respective locations are determined based on the expression $$a = b\sqrt{\frac{1}{\cos^2\theta} - 1},$$

where a is one of the respective locations, b is the offset distance, and θ is the angle.

At step 504, process 500 (e.g., using one or more components in system 400 (FIG. 4)) generate for display the visual field testing pattern. For example, the system may generate for display the visual field testing pattern on the head-mounted display.

At step 506, process 500 (e.g., using one or more components in system 400 (FIG. 4)) retrieves data from a tilt sensor. For example, the system may retrieve data from a tilt sensor for detecting degrees of head tilt of a user wearing the head-mounted display. The tilt sensor can be, for example, located at the head-mounted display.

At step 508, process 500 (e.g., using one or more components in system 400 (FIG. 4)) determines a degree of head tilt of a user. For example, the system may determine, based on the data retrieved from the tilt sensor, a degree of head tilt of the user.

At step 510, process 500 (e.g., using one or more components in system 400 (FIG. 4)) compare the degree of head tilts. For example, the system may compare, using the control circuitry, the degree of head tilt of the user to a first threshold degree. In another example, process 500 can compare the degree of head tilt of the user to a second threshold degree and in response to the degree of head tilt of the user meeting or exceeding the second threshold degree, automatically adjusts a respective location of a stimulus of the plurality of icons in the visual field of the head-mounted display by a first amount. For example, the first amount can be is based on a distance of the icon from a centerpoint of the visual field of the head-mounted display and a direction of the head tilt of the user.

At step 512, process 500 (e.g., using one or more components in system 400 (FIG. 4)) generate a recommendation to the user. For example, the system may generate for display a recommendation to the user. For example, the recommendation can be displayed on the head-mounted display. The generation can also be in response to the degree of head tilt of the user meeting or exceeding the first threshold degree.

It is contemplated that the steps or descriptions of FIG. 5 may be used with any other embodiment of this disclosure. In addition, the steps and descriptions described in relation to FIG. 5 may be done in alternative orders or in parallel to further the purposes of this disclosure. For example, each of these steps may be performed in any order, in parallel, or simultaneously to reduce lag or increase the speed of the system or method. Furthermore, it should be noted that any of the devices or equipment discussed in relation to FIGS. 1-3 could be used to perform one or more of the steps in FIG. 5.

Figure 6:
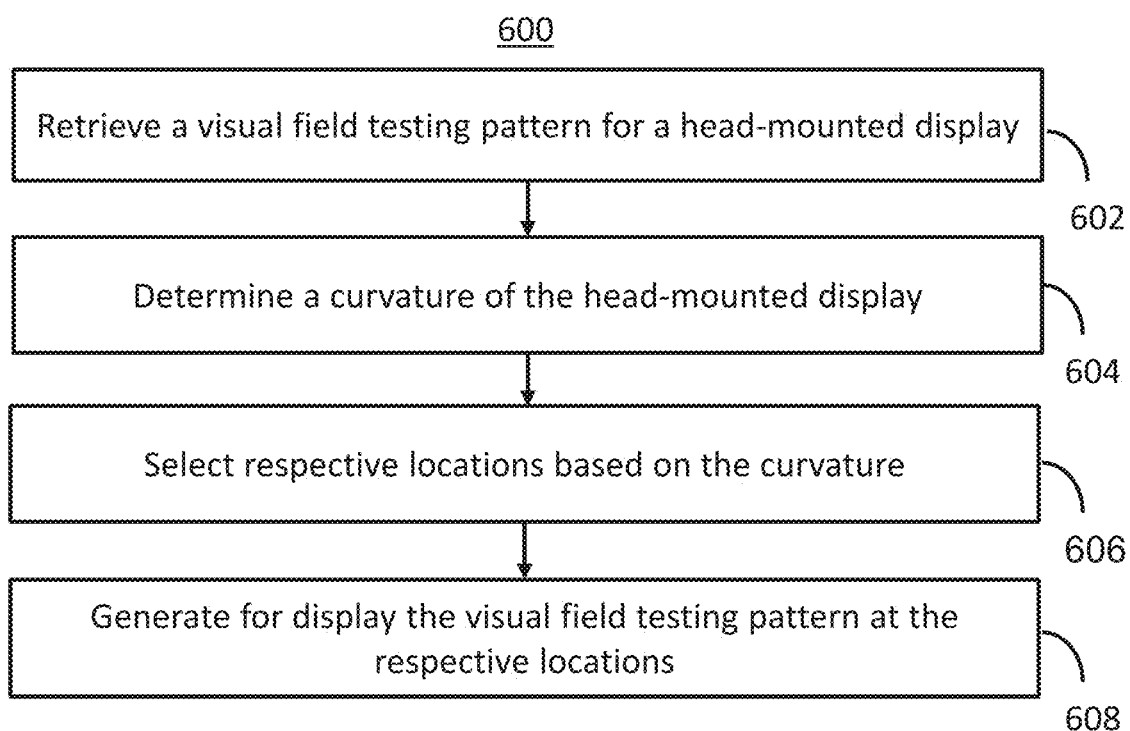
FIG. 6 is a process flow diagram for accurately replicating a visual field testing pattern from a curved surface on a flat surface in accordance with certain aspects of the present disclosure.

FIG. 6 is a process flow diagram for accurately replicating a visual field testing pattern from a curved surface on a flat surface. For example, process 600 may represent the steps taken by one or more devices, as shown in FIGS. 1A-1C, when providing visual field testing using a head-mounted display.

At step 602, process 600 (e.g., using one or more components in system 400 (FIG. 4) retrieves a visual field testing pattern for a head-mounted display. For example, the system may retrieve a visual field testing pattern for a head-mounted display, wherein the visual field testing pattern comprises stimuli that are displayed at respective locations in a visual field of the head-mounted display.

At step 604, process 600 (e.g., using one or more components in system 400 (FIG. 4)) determines a curvature of the head-mounted display. For example, the system may determine a curvature of the head-mounted display based on receiving data from one or more sensors. Additionally or alternatively, the system may receive settings based on an initial calibration (e.g., an automatic calibration or a manual calibration) when the system is activated. Additionally or alternatively, the system may input a model or serial number (or other identifier) for the head-mounted display into a look-up table listing curvatures for the model or serial number.

Additionally or alternatively, in some embodiments, the system may determine an offset distance of the head-mounted display based on receiving data from one or more sensors. Additionally or alternatively, the system may receive settings based on an initial calibration (e.g., an automatic calibration or a manual calibration) when the system is activated indicating the offset distance. Additionally or alternatively, the system may input a model or serial number (or other identifier) for the head-mounted display into a look-up table listing offset distance for the model or serial number.

At step 606, process 600 (e.g., using one or more components in system 400 (FIG. 4)) selects the respective locations based on the curvature. For example, the system may automatically adjust the respective locations based on the curvature and/or offset distance determined by the system. In some embodiments, the system may receive the curvature and/or offset distance (e.g., via input entered into a user terminal (e.g., user terminal 424 (FIG. 4)) and adjust the respective locations accordingly.

At step 608, process 600 (e.g., using one or more components in system 400 (FIG. 4)) generates for display the visual field testing pattern on the head-mounted display. For example, in generating the visual field testing pattern, the respective locations of the stimuli can be located in a row on the visual field. In another example, the respective locations can correspond to respective projections of points corresponding to different viewing angles along a curved surface onto a flat surface.

It is contemplated that the steps or descriptions of FIG. 6 may be used with any other embodiment of this disclosure. In addition, the steps and descriptions described in relation to FIG. 6 may be done in alternative orders or in parallel to further the purposes of this disclosure. For example, each of these steps may be performed in any order, in parallel, or simultaneously to reduce lag or increase the speed of the system or method. Furthermore, it should be noted that any of the devices or equipment discussed in relation to FIGS. 1-3 could be used to perform one or more of the steps in FIG. 6.

Figure 7:
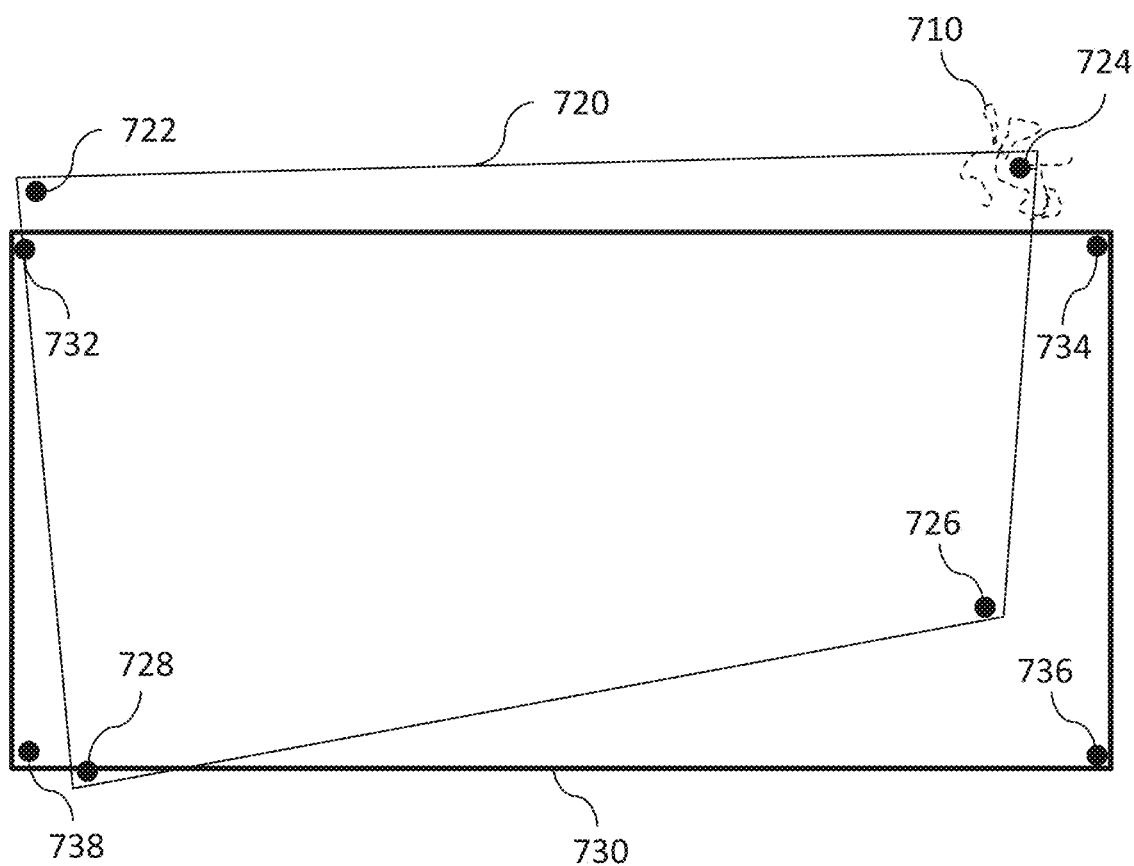
FIG. 7 is a diagram illustrating an exemplary relationship between a virtual plane and a display plane as used to calibrate a head-mounted display, in accordance with certain aspects of the present disclosure.

FIG. 7 illustrates a simplified diagram depicting an exemplary relationship between a virtual plane and a display plane as may be used to calibrate a head-mounted display. As described further herein, the disclosed systems may generate a calibration pattern comprising a number of stimuli (e.g., one or more graphical elements, referred to herein as "icons") for display at the head-mounted display.

The calibration may take many forms and may comprises one or more stimuli being displayed in series and/or in parallel. The system may display a pattern in which the stimuli are displayed at particular positions. The positions may be defined by the system in terms of a height, width and/or viewing angle. The system may generate the stimuli at the extremes of the visual field in order to achieve the best calibration. For example, the system may display the stimuli in one or more corners of the visual field in order to receive the best measurement for calibrating a user's gaze location on a single fixation point (e.g., a centerpoint in the visual field).

The example of FIG. 7 depicts a simplified representation showing a viewing plane 730 having a number of stimuli (e.g. edge stimuli 732, 734, 736, 738) that may be seen by a user. However, for example due to improper wearing or other errors, eye tracking data obtained from a user viewing any one of these edge stimuli may not correspond to where the eye tracking data would be expected based on where the edge stimulus is displayed by the head-mounted display. Example eye tracking data 710 is shown corresponding to edge stimulus 734. The eye tracking data is depicted as a dashed line representing the path of the eye over its acquisition time. In this example, even though the system generates edge stimulus 734, the eye tracking data generally surrounds the perceived edge point 724.

In some embodiments, the system may retrieve calibration data of a given interval. The use of the given interval allows the system to normalize data during this time to remove outlier that may occur as a natural result of the calibration process. For example, the edge point can be determined by receiving eye tracking data over periods of time referred to herein as edge calibration periods. The edge calibration periods may be, for example, one second, five seconds, etc. In some implementations, eye tracking data may be averaged over such periods of time to generate an average location. This process may be repeated for a number of edge stimuli, with four shown in the example of FIG. 7. Thus, as depicted, edge points 732, 734, 736, and 738 generate corresponding points 722, 724, 726, and 728. While four points are shown, in other embodiments, other numbers of points may be used, for example, three, five, eight, etc. in some embodiments, the system may generate edge stimuli on edges of the field of view of the head-mounted display. For example, along one or more of the left, right, upper, or lower edges. In certain embodiments, edge stimuli may be generated at the corners of the field, for example, upper left, upper right, lower left, or lower right. It is also contemplated that stimuli may be generated anywhere within the field of view stimuli may be generated anywhere within the field of view such that the presently described calibrations may be performed.

As part of various technical solutions that address the disclosed shortcomings of conventional calibration methods, certain disclosed embodiments describe how the system may relate and assess differences between what is displayed and what the user sees. Similar to how the edge stimuli may define a display plane 730 (i.e., a plane established by the system where the edge stimuli are displayed on), the edge points may also define a virtual plane 720. The system may calculate a projective transform matrix based on the edge eye tracking data that converts any location in virtual plane 720 to display plane 730. Thus, as described further below, stimuli or other calibration patterns may be generated by the head-mounted display and the obtained eye tracking data may be mapped back onto the display plane for comparison with the calibration pattern.

The system may calculate a projective transform matrix that is especially useful for a general transformation (e.g., one that does not force parallelism to be observed as such may not be the case when formerly parallel stimuli are viewed by a person). The below example illustrates how the system may generate and/or utilize a projective transform matrix for a coordinate transformation between the two planes 720 and 730:

$$\begin{pmatrix} a_1 & a_2 & b_1 \\ a_3 & a_4 & b_2 \\ c_1 & c_2 & 1 \end{pmatrix} \begin{pmatrix} x \\ y \\ 1 \end{pmatrix} = \begin{pmatrix} x' \\ y' \\ 1 \end{pmatrix}.$$

In the above matrix equation, the 2×2 "a" submatrix is a rotation matrix, the 2×1 "b" submatrix is a translation vector, and the 1×2 "c" submatrix is a projection vector. The x,y elements correspond to the x,y coordinates of the edge stimulus in the display plane (e.g., edge stimulus 734) and the x',y' elements corresponding to the x,y coordinates of the point in the virtual plane (e.g., point 724). To apply the projective transform metric, the system may execute pseudocode such as shown in FIG. 10.

For example, the projective transformation can be represented as transformation of an arbitrary quadrangle (i.e. system of four points) into another one. Alternatively or additionally, the system may use a transform based on a different number of points. For example, the system may use an affine transformation, which is a transformation of a triangle. The system may select the type of transform based on the number of stimuli generated. The system may select the number of stimuli generated based on one or more criteria. For example, the system may determine a number of stimuli needed to achieve a determined amount of accuracy and/or meet a particular threshold level of precision. The system may likewise select the number of stimuli based on a type of test, amount of calibration needed, and/or a frequency of calibration.

For example, the system may determine that a four point (e.g., projective transform) calibration is used at the initiation of the user of a head mounted device. The system may then determine (e.g., using a hierarchy of criteria) whether an additional calibration needs to be performed, and if so, how many stimuli are required to be displayed.

Figure 8:
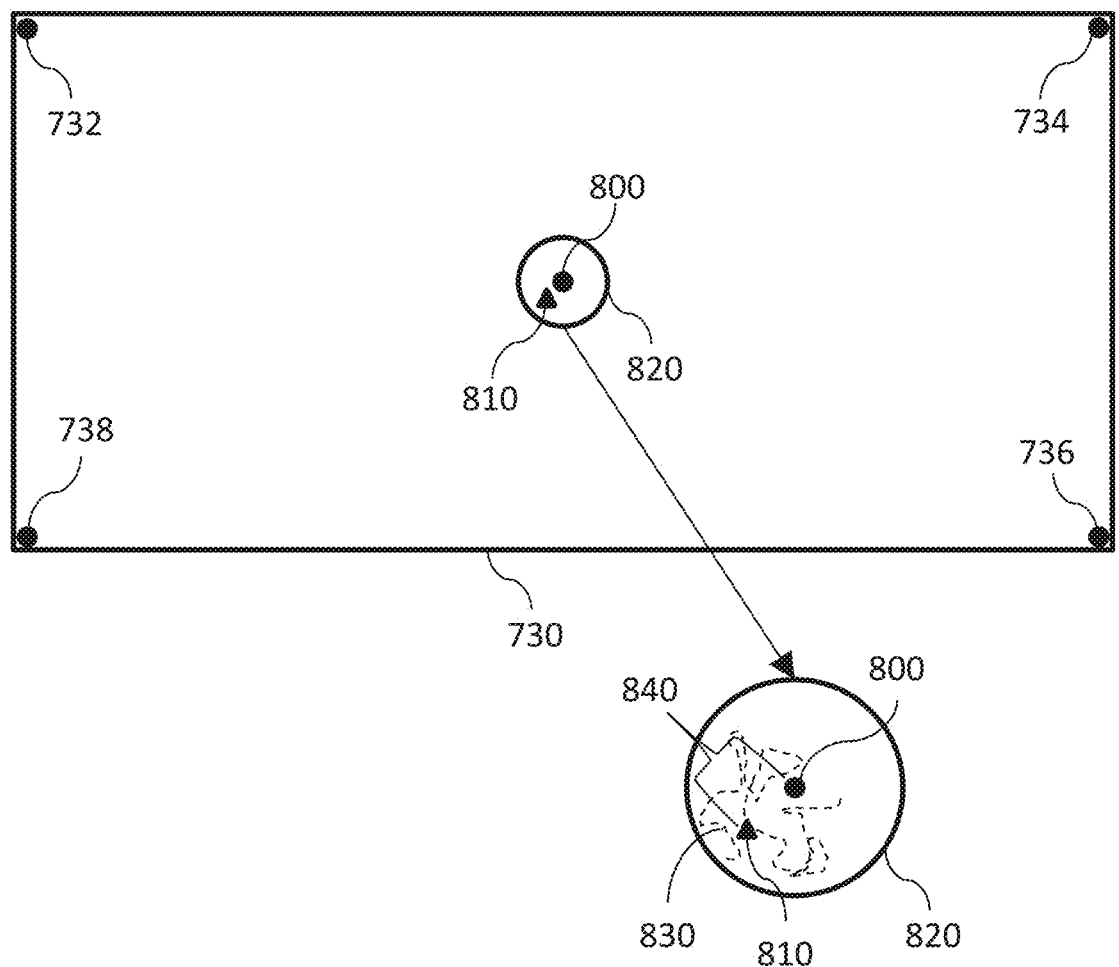
FIG. 8 is a diagram illustrating an exemplary central point and boundary as used to generate a calibration score, in accordance with certain aspects of the present disclosure.

FIG. 8 illustrates a simplified diagram depicting an exemplary central point and boundary as used to generate a calibration score. In some implementations, it may be of more interest to base a calibration off of a point more central in a field of view, as such is where most visual testing patterns are displayed. The system may generate for display a center stimulus 800 on the head-mounted display at a center location. This system may also receive center eye tracking data during a center calibration period, similar to the edge calibration period(s) described above. The calculated point in the virtual plane may be transformed to what is referred to herein as a "gaze location" in the display plane by the system utilizing the projective transform matrix. The system may generate a calibration score based on a difference 840 (e.g., a delta in pixels, mm, or other similar distance metrics) between the center stimulus 800 and the gaze location 810. The inset shows this example in greater detail and includes exemplary eye tracking data 830 and the difference 840 between center stimulus 800 and gaze location 810. Also, in various embodiments the difference 840 may be similarly calculated the virtual plane 720 via a determination of equivalent points for the center stimulus and gaze location. In this way, is contemplated that any combination of points may be utilized in either plane and related to each other via the projective transform matrix to calculate differences, locations relative to a boundary (as described below), etc.

In some implementations, the system may assess the accuracy of the calibration based on whether the gaze location and/or eye tracking data is within a prescribed boundary. For example, as shown in FIG. 8, the system may generate boundary 820. In some implementations, such a boundary may be a circle having a given radius from the center stimulus 800, but other boundary shapes such as square, hexagonal, etc. may be used. While in some implementations the boundary may be visually displayed by the head-mounted display, this is not necessary and instead the boundary may merely reside as coordinates or other boundary defining algorithm in computer memory. Accordingly, the system may determine the calibration score based on the size (e.g. radius) of the boundary.

As previously mentioned, the calibration score may be indicative of the confidence in the calibration. In this way, should a calibration be determined by the system to fail (e.g., the gaze location being outside the radius of the boundary), the system may repeat at least a portion of the calibration (e.g., the acquiring of edge eye tracking data, center eye tracking data, and/or calculation of the projective transform matrix), but making the size of the boundary larger (e.g., a larger radius boundary). For example, in one embodiment if the gaze location is calculated to be within the first (or initial) boundary generated, the calibration may be assigned a score of 100 (perhaps corresponding to the best possible calibration). If that calibration attempt were to have failed, then, for example, the radius of the boundary may be increased 20% and if that calibration succeeds then it may be assigned a score of 90. Any such relationship between boundary size and calibration score may be used by the system, as implemented by a person of skill.

The system may also determine, based on the gaze location, whether a user is looking at the center location. Such a determination may be made by the system, for example, if the gaze location is outside of a bounding box, an area defined by the edge stimuli, etc. Another related implementation can further refine the calibration is not allowing large, sustained deviations in the eye tracking data, even if the average location is within one of the above-described boundaries. For example, the system may determine that the user is not looking at the center location based on whether at least a portion of the center eye tracking data deviates from the gaze location more than a spatial deviation threshold and for longer than a temporal deviation threshold. As one specific example, the spatial deviation threshold may be any distance outside the boundary, but may also be a larger boundary (e.g., 1.1×, 1.5× the radius of the present boundary). While a brief excursion may be allowed, the temporal deviation threshold may be set by the system to be, for example, 1 ms, 10 ms, 100 ms, etc. In this way, the system would determine that the calibration failed if the user's gaze drifted, for example, far to the left and stayed there, indicating a possible loss of focus or attention on the calibration process.

Figure 9:
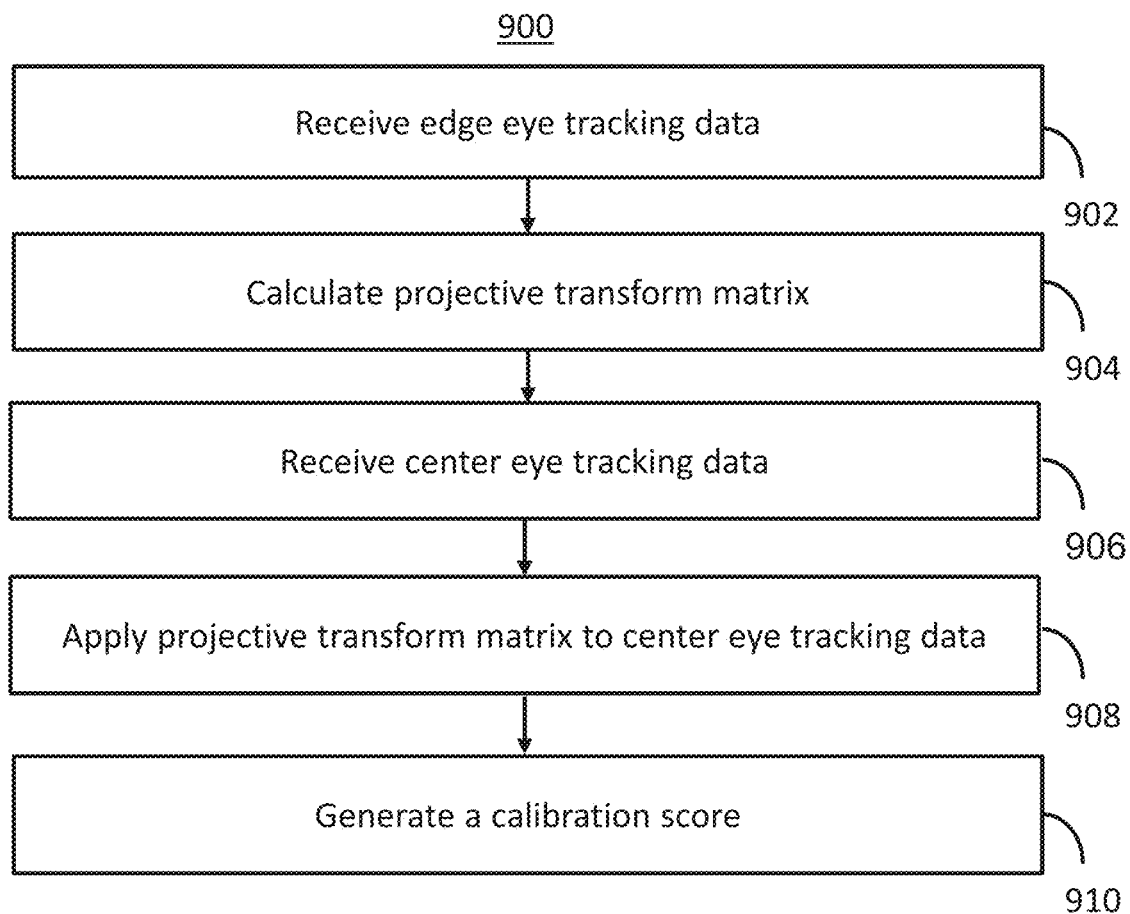
FIG. 9 is a process flow diagram for calibrating a head-mounted display, in accordance with certain aspects of the present disclosure.

FIG. 9 is a process flow diagram for calibrating a head-mounted display. For example, process 900 may represent steps taken by one or more devices, as shown in FIGS. 1A-1E, when calibrating the head-mounted display.

At step 902, process 900 (e.g., using one or more components in system 400 (FIG. 4)) receives edge eye tracking data. For example, the system may receive edge eye tracking data during edge calibration periods. Additionally or alternatively, the system may generate for display a number of edge stimuli on the head-mounted display. Additionally or alternatively, the system may generate edge stimuli on edges or of a field of view of the head-mounted display.

At step 904, process 900 (e.g., using one or more components in system 400 (FIG. 4)) calculates a projective transform matrix. For example, the system may calculate a projective transform matrix based on the edge eye tracking data. For example, the system may use pseudocode 1000 (FIG. 10) and/or the process described in FIG. 7.

At step 906, process 900 (e.g., using one or more components in system 400 (FIG. 4)) receives center eye tracking data. For example, the system may receive center eye tracking data during a center calibration period. Additionally or alternatively, the system may generate for display a center stimulus on the head-mounted display at the center location. Additionally or alternatively, the system may generate a boundary around the center stimulus and may display the boundary at the head display.

At step 908, process 900 (e.g., using one or more components in system 400 (FIG. 4)) applies a projective transform matrix to the center eye tracking data. For example, the system may apply the projective transform matrix to the center eye tracking data to determine a gaze location.

At step 910, process 900 (e.g., using one or more components in system 400 (FIG. 4)) generates a calibration score. For example, the system may generate a calibration score based on a difference between a central location and the gaze location. The calibration score may be indicative of the accuracy of an eye test performed with the head-mounted display. Additionally or alternatively, the system may determine, based on the difference, whether the gaze location is inside the boundary. Additionally or alternatively, the calibration score may be based on a size of the boundary. Additionally or alternatively, the system, in response to the difference indicating that the gaze location is outside the boundary, may repeat at least a portion of the calibration, wherein the size of the boundary is larger. Additionally or alternatively, the system may determine whether a user is looking at the center location based on the gaze location. In response to the determination that the user is not looking at the center location, the system may repeat at least a portion of the calibration. Additionally or alternatively, the determination by the system that the user is not looking at the center location may require that at least a portion of the center eye tracking data deviates from the gaze location more than a spatial deviation threshold and for longer than a temporal deviation threshold.

It is contemplated that the steps or descriptions of FIG. 9 may be used with any other embodiment of this disclosure. In addition, the steps and descriptions described in relation to FIG. 9 may be done in alternative orders or in parallel to further the purposes of this disclosure. For example, each of these steps may be performed in any order, in parallel, or simultaneously to reduce lag or increase the speed of the system or method. Furthermore, it should be noted that any of the devices or equipment discussed in relation to FIGS. 1A-1E could be used to perform one or more of the steps in FIG. 9.

FIG. 10 is illustrative pseudocode for calibrating a head-mounted display in accordance with certain aspects of the present disclosure. For example, pseudocode 1000 represents illustrative pseudocode for calculating a projective transform matrix as described herein. The below example illustrates how the system may generate and/or utilize a projective transform matrix for a coordinate transformation between the two planes (e.g., planes 720 and 730 of FIG. 7). For example, pseudocode 1000 may generate values for 4×4 described in FIG. 7. In such cases, the points identified in pseudocode 1000 may correspond to the x,y coordinates of the edge stimulus in the display plane (e.g., edge stimulus 734) and x,y coordinates of the point in the virtual plane (e.g., point 724).

The above-described embodiments of the present disclosure are presented for purposes of illustration and not of limitation, and the present disclosure is limited only by the claims which follow. Furthermore, it should be noted that the features and limitations described in any one embodiment may be applied to any other embodiment herein, and flowcharts or examples relating to one embodiment may be combined with any other embodiment in a suitable manner, done in different orders, or done in parallel. In addition, the systems and methods described herein may be performed in real time. It should also be noted that the systems and/or methods described above may be applied to, or used in accordance with, other systems and/or methods.

In the following, further features, characteristics, and exemplary technical solutions of the present disclosure will be described in terms of items that may be optionally claimed in any combination:

1. A method, the method comprising: retrieving a visual field testing pattern for a head-mounted display; and generating for display the visual field testing pattern on the head-mounted display.
2. The method of any of the preceding items, wherein the visual field testing pattern comprising stimuli that are displayed at respective locations in a visual field of the head-mounted display.
3. The method of any of the preceding items, further comprising retrieving data from a tilt sensor, located at the head-mounted display, for detecting degrees of head tilt of a user wearing the head-mounted display; determining, based on the data retrieved from the tilt sensor, a degree of head tilt of the user; and comparing, the degree of head tilt of the user to a first threshold degree.
4. The method of any of the preceding items, further comprising generating for display, on the head-mounted display, a recommendation to the user in response to the degree of head tilt of the user meeting or exceeding the first threshold degree.
5. The method of any of the preceding items, further comprising: comparing the degree of head tilt of the user to a second threshold degree; and in response to the degree of head tilt of the user meeting or exceeding the second threshold degree, automatically adjusting a respective location of a stimulus of the stimuli in the visual field of the head-mounted display by a first amount.
6. The method of any of the preceding items, wherein the first amount is based on a distance of the stimulus from a centerpoint of the visual field of the head-mounted display and a direction of the head tilt of the user.
7. The method of any of the preceding items, wherein the respective location of the stimulus is defined by a first directional component and a second directional component, and wherein the first directional component is adjusted by a cosine of the degree of head tilt of the user and the second directional component is adjusted by a sine of the degree of head tilt of the user.
8. The method of any of the preceding items, wherein the respective locations of the stimulus are located in a row on the visual field, and wherein the respective locations correspond to respective projections of points corresponding to different viewing angles along a curved surface onto a flat surface.
9. The method of any of the preceding items, wherein the respective locations are determined based on an offset distance of the head-mounted display and an angle to respective points on the visual testing machine.
10. The method of any of the preceding items, wherein the respective locations are determined based on the expression $$a = b\sqrt{\frac{1}{\cos^2\theta} - 1},$$

where a is one of the respective locations, b is the offset distance, and q is the angle.
11. The method of any of the preceding items, further comprising determining a curvature of the head-mounted display and selecting the respective locations based on the curvature.
12. The method of any of the preceding items, further comprising determining an offset distance of the head-mounted display and selecting the respective locations based on the offset distance.
13. The method of any of the preceding items, further comprising determining a centerpoint of the head-mounted display and selecting the respective locations based on the centerpoint.
14. A method for calibrating a head-mounted display, the method comprising: receiving edge eye tracking data during a plurality of edge calibration periods; calculating a projective transform matrix based on the edge eye tracking data; receiving center eye tracking data during a center calibration period; applying the projective transform matrix to the center eye tracking data to determine a gaze location; and generating a calibration score based on a difference between a center location and the gaze location.
15: The method of Item 14, further comprising: generating for display stimuli on the head-mounted display; and generating for display a center stimulus on the head-mounted display at the center location.
16: The method of Item 14 or any of the preceding items that depend therefrom, wherein the stimuli are generated on edges of a field of view of the head-mounted display.
17: The method of Item 14 or any of the preceding items that depend therefrom, wherein the stimuli are generated at corners of a field of view of the head-mounted display.
18: The method of Item 14 or any of the preceding items that depend therefrom, wherein the calibration score is indicative of the accuracy of an eye test performed with the head-mounted display.
19: The method of Item 14 or any of the preceding items that depend therefrom, further comprising: generating a boundary around the center stimulus; determining, based on the difference, whether the gaze location is inside the boundary; and determining the calibration score based on a size of the boundary.
20: The method of Item 14 or any of the preceding items that depend therefrom, further comprising displaying the boundary at the head mounted display.
21: The method of Item 14 or any of the preceding items that depend therefrom, further comprising: in response to the difference indicating that the gaze location is outside the boundary, repeating at least a portion of the calibration, wherein the size of the boundary is larger.
22: The method of Item 14 or any of the preceding items that depend therefrom, further comprising: determining whether a user is looking at the center location based on the gaze location; and in response to the determination that the user is not looking at the center location, repeating at least a portion of the calibration.
23: The method of Item 14 or any of the preceding items that depend therefrom, wherein the determination that the user is not looking at the center location requires that at least a portion of the center eye tracking data deviates from the gaze location more than a spatial deviation threshold and for longer than a temporal deviation threshold.
24: A system for calibrating head-mounted displays, the system comprising: a head-mounted display; inward directed sensors, located at the head-mounted display, configured to track pupil movement; storage circuitry configured to store a plurality of icons that are displayed at respective locations in a visual field of the head-mounted display; and control circuitry configured to: to perform operations comprising those of any of items 1-23.

25: A tangible, non-transitory, machine-readable medium storing instructions that, when executed by a data processing apparatus, cause the data processing apparatus to perform operations comprising those of any of items 1-23.

26. A system comprising: one or more processors; and memory storing instructions that, when executed by the processors, cause the processors to effectuate operations comprising those of any of items 1-23.

27. A system comprising means for performing any of items 1-23.

The present disclosure contemplates that the calculations disclosed in the embodiments herein may be performed in a number of ways, applying the same concepts taught herein, and that such calculations are equivalent to the embodiments disclosed.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" (or "computer readable medium") refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" (or "computer readable signal") refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The subject matter described herein can be embodied in systems, apparatus, methods, computer programs and/or articles depending on the desired configuration. Any methods or the logic flows depicted in the accompanying figures and/or described herein do not necessarily require the particular order shown, or sequential order, to achieve desirable results. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. The implementations described above can be directed to various combinations and subcombinations of the disclosed features and/or combinations and subcombinations of further features noted above. Furthermore, above described advantages are not intended to limit the application of any issued claims to processes and structures accomplishing any or all of the advantages.

Additionally, section headings shall not limit or characterize the invention(s) set out in any claims that may issue from this disclosure. Further, the description of a technology in the "Background" is not to be construed as an admission that technology is prior art to any invention(s) in this disclosure. Neither is the "Summary" to be considered as a characterization of the invention(s) set forth in issued claims. Furthermore, any reference to this disclosure in general or use of the word "invention" in the singular is not intended to imply any limitation on the scope of the claims set forth below. Multiple inventions may be set forth according to the limitations of the multiple claims issuing from this disclosure, and such claims accordingly define the invention(s), and their equivalents, that are protected thereby.

What is claimed is:

1. A system for calibrating head-mounted displays utilizing a projective transform matrix, the system comprising:
   a head-mounted display;
   inward directed sensors, located at the head-mounted display, configured to track pupil movement;
   storage circuitry configured to store a plurality of icons that are displayed at respective locations in a visual field of the head-mounted display; and
   control circuitry configured to:
   generate for display a plurality of edge icons on the head-mounted display;
   receive, via the inward directed sensors, edge eye tracking data during a plurality of edge calibration periods corresponding to the display of the plurality of edge icons;
   calculate the projective transform matrix based on the edge eye tracking data;
   generate for display a center icon on the head-mounted display at a center location;
   receive center eye tracking data during a center calibration period;
   apply the projective transform matrix, calculated based on the edge eye tracking data, to the center eye tracking data to determine a gaze location; and
   generate a calibration score based on a difference between the center location and the gaze location.

2. A method for calibrating a head-mounted display, the method comprising:
   receiving, via one or more inward directed sensors of the head-mounted display, edge eye tracking data during a plurality of first calibration periods, wherein the plurality of first calibration periods are periods during which eye tracking data is collected for edge stimuli displayed on the head-mounted display;
   calculating, based on the edge eye tracking data, a projective transform matrix indicating coordinate transformations between a first plane and a second plane;
   receiving center eye tracking data during a second calibration period, wherein the second calibration period is a period during which eye tracking data is collected for a center stimulus displayed on the head-mounted display;
   applying the projective transform matrix, calculated based on the edge eye tracking data, to the center eye tracking data to determine a gaze location; and
   generating a calibration score based on a difference between a center location and the gaze location.

3. The method of claim 2, further comprising:
   generating, for display, edge stimuli on the head-mounted display; and
   generating, for display, a center stimulus on the head-mounted display at the center location.

4. The method of claim 3, wherein the edge stimuli are generated on edges of a field of view of the head-mounted display.

5. The method of claim 4, wherein the edge stimuli are generated at corners of a field of view of the head-mounted display.

6. The method of claim 3, wherein the calibration score is indicative of an accuracy of an eye test performed with the head-mounted display.

7. The method of claim 3, further comprising: generating a boundary around the center stimulus;
   determining, based on the difference, whether the gaze location is inside the boundary; and determining the calibration score based on a size of the boundary.

8. The method of claim 7, further comprising displaying the boundary at the head-mounted display.

9. The method of claim 7, further comprising:
   in response to the difference indicating that the gaze location is outside the boundary, updating the boundary to be a larger boundary and determining the calibration score based on an updated size of the updated boundary.

10. The method of claim 3, further comprising:
    determining whether a user is looking at the center location based on the gaze location; and in response to the determination that the user is not looking at the center location, repeating
    at least a portion of a calibration process by updating the edge eye tracking data via an additional collection of eye tracking data for edge stimuli displayed on the head-mounted display and updating the projective transform matrix based on the updated edge eye tracking data.

11. The method of claim 10, wherein the determination that the user is not looking at the center location requires that at least a portion of the center eye tracking data deviates from the gaze location more than a spatial deviation threshold and for longer than a temporal deviation threshold.

12. One or more non-transitory machine-readable media storing instructions that, when executed by one or more processors, cause operations comprising:
    receiving, via one or more inward directed sensors of a head-mounted display, edge eye tracking data during a plurality of first calibration periods, wherein the plurality of first calibration periods are periods during which eye tracking data is collected for edge stimuli displayed on the head-mounted display;
    calculating a projective transform matrix based on the edge eye tracking data;
    receiving center eye tracking data during a second calibration period, wherein the second calibration period is a period during which eye tracking data is collected for a center stimulus displayed on the head-mounted display;
    applying the projective transform matrix, calculated based on the edge eye tracking data, to the center eye tracking data to determine a gaze location; and
    generating a calibration score based on a difference between a center location and the gaze location.

13. The one or more non-transitory machine-readable media of claim 12, further comprising:
    generating, for display, edge stimuli on the head-mounted display; and
    generating, for display, a center stimulus on the head-mounted display at the center location.

14. The one or more non-transitory machine-readable media of claim 13, wherein the edge stimuli are generated on edges of a field of view of the head-mounted display.

15. The one or more non-transitory machine-readable media of claim 14, wherein the edge stimuli are generated at corners of a field of view of the head-mounted display.

16. The one or more non-transitory machine-readable media of claim 13, further comprising:

generating a boundary around the center stimulus;

determining, based on the difference, whether the gaze location is inside the boundary; and determining the calibration score based on a size of the boundary.

17. The one or more non-transitory machine-readable media of claim 16, further comprising displaying the boundary at the head-mounted display.

18. The one or more non-transitory machine-readable media of claim 16, further comprising:

in response to the difference indicating that the gaze location is outside the boundary, updating the boundary to be a larger boundary and determining the calibration score based on an updated size of the updated boundary.

19. The one or more non-transitory machine-readable media of claim 13, further comprising:

determining whether a user is looking at the center location based on the gaze location; and in response to the determination that the user is not looking at the center location, repeating at least a portion of a calibration process by updating the edge eye tracking data via an additional collection of eye tracking data for edge stimuli displayed on the head-mounted display and updating the projective transform matrix based on the updated edge eye tracking data.

20. The one or more non-transitory machine-readable media of claim 19, wherein the determination that the user is not looking at the center location requires that at least a portion of the center eye tracking data deviates from the gaze location more than a spatial deviation threshold and for longer than a temporal deviation threshold.

* * * * *